United States Patent [19]

Sato et al.

[11] Patent Number: 5,187,062
[45] Date of Patent: Feb. 16, 1993

[54] METHOD FOR DETECTING AND MEASURING FGF

[75] Inventors: Yuji Sato, Tokyo, Japan; Henry G. Friesen, Winnipeg, Canada

[73] Assignee: Takeda Chemical Industries, Ltd., Osaka, Japan

[21] Appl. No.: 345,220

[22] Filed: Apr. 28, 1989

[30] Foreign Application Priority Data

Dec. 7, 1988 [JP] Japan .................................. 63-310856

[51] Int. Cl.⁵ .............................................. C12Q 1/00
[52] U.S. Cl. ...................... 435/7.94; 435/28; 436/501; 436/517
[58] Field of Search ...................... 435/7, 28; 436/501, 436/517

[56] References Cited

U.S. PATENT DOCUMENTS 4,652,532  3/1987  Bain et al. ............................ 436/501

OTHER PUBLICATIONS

Klagsbrun et al—Proc. Natl. Acad. Sci.—vol. 82 (Feb. 1985) pp. 805-809.
S. L. Mossoglia et al. Journal of Cellular Physiology, 132, 531-537 (1987).
D. Gospodarowicz et al. Journal of Cellular Physiology, 128, 475-484 (1986).
M. L. Brandi et al. The New England Journal of Medicine, 314, 1287-1293 (1987).

*Primary Examiner*—Sam Rosen
*Attorney, Agent, or Firm*—David G. Conlin; Ronald I. Eisenstein

[57] ABSTRACT

A sandwich method, in which heparin coupled to a carrier, a sample and an antibody labeled with a labeling agent, brings about a high sensitivity for detecting and/or measuring FGF.

3 Claims, 4 Drawing Sheets

METHOD FOR DETECTING AND MEASURING FGF

The present invention relates to a method for detecting and/or measuring fibroblast growth factor (hereinafter also abbreviated FGF) using a sandwich technique.

There are two types of FGF: basic FGF, which has a basic isoelectric point, and acidic FGF, which has an acidic isoelectric point; the amino acid sequence of both types is known [F. Esch et al., Proc. Natl. Acad. Sci. USA, 85, 6507(1985); K. A. Thomas et al., Proc Natl. Acad. Sci. USA, 82, 6409 (1985)].

FGF exhibits a growth promoting activity on 3T3 cells and mesoderm-derived cells, including vascular endothelial cells, in vitro and an angiogenic activity in vivo [D. Gospodarowicz et al., Endocrine Reviews, 8,95(1987)]. In particular, the angiogenic activity of FGF, in combination with the cell growth promoting activity, can be used in therapeutic drugs for wounds and burns, and preventive/therapeutic drugs for thrombosis, arteriosclerosis and other diseases.

FGF is found in nature in only extremely small quantities; it has been very difficult, due to various limitations, to detect natural FGF from human tissues. In addition, no method has yet been developed which permits easy quantitative determination of FGF.

For these reasons, much information of FGF, indispensable for developing FGF as a pharmaceutical, remains unknown.

Obtaining information on FGF, e.g. its production and distribution mechanisms in vivo, will therefore facilitate development of FGF as a pharmaceutical.

Also, accurate quantitative determination of FGF is important in purifying this protein from transformed cells. Furthermore, it is very important to monitor blood FGF levels in FGF-administered animals; however, such measurement in impossible by conventional methods, all of which use 3T3 cells, due to sample contamination with blood serum. Conventionally, FGF measurement has been achieved by starving 3T3 cells in reduced serum concentrations to suppress DNA synthesis, adding FGF to the cells, and calculating the degree of recovery of DNA synthesis capability. This method, however, is faulty in that the use of cells necessitates delicate micromanipulation and produces wide errors of measurement, and that much time is taken to obtain results. It has therefore been hoped that a simple and reliable method of measuring FGF would be developed to accomplish these purposes.

In the light of these circumstances, the present inventors conducted various investigations with the aim of finding a practical means of FGF measurement, and found that FGF can be measured to high sensitivity by using heparin as a ligand coupled with a carrier in the sandwich technique wherein two ligands are used. The present inventors made further investigations based on this finding, in developing the present invention.

Accordingly, the present invention involves a method for detecting and/or measuring FGF by a sandwich technique using heparin coupled to a carrier, a sample and an antibody labeled with a labeling agent.

As the method of detecting and/or measuring FGF the present invention may be based on radioimmunoassay (hereinafter also abbreviated RIA) or enzyme immunoassay (hereinafter also abbreviated EIA).

The FGF may be any FGF, as long as it is derived from warm-blooded animals, and may also be an FGF mutein.

Therefore, in the present specification, FGF includes its mutein, unless otherwise stated.

Both types of FGF, i.e. acidic FGF (hereinafter also abbreviated a FGF) and basic FGF (hereinafter also abbreviated bFGF) are included; basic FGF however is preferred.

THE FGF may be of natural derivation, or may be produced by gene engineering technology.

Examples of mammalian-derived aFGF include bovine aFGF [K. A. Thomas et al., Proc. Natl. Acad. Sci. USA, 81, 357 (1984)] and human aFGF [G. Gimenez-Gallego et al., Biochem. Biophys. Res. Commun., 138, 611 (1986)].

Examples of mammalian-derived bFGF include bovine bFF [Proc. Natl. Acad. Sci. USA, 82, 6507 (1985)] and human bFGF [European Patent Publication No. 237966; European Molecular Biology Organization (EMBO) Journal, 5,2523(1986)].

The above-mentioned mutein refers to a peptide or protein with a mutated amino acid sequence; the mutation includes amino acid addition, deletion of a constituent amino acid and amino acid replacement by other amino acid.

Examples of amino acid addition include addition of at least one amino acid.

Examples of constituent amino acid deletion include a lack of at least one FGF-constituent amino acid.

Examples of amino acid replacement by other amino acid include replacement of at least one FGF-constituent amino acid by other amino acid.

The "at least one amino acid" in the mutein resulting from the addition of at least one amino acid to FGF does not include methionine derived from the initiation codon or signal peptide used for peptide expression.

Any number of amino acids may be added, as long as the properties of FGF are maintained. Examples of preferred amino acids to be added include partial or entire amino acid sequences of proteins recognized as homologous with FGF and having similar activities.

In the mutein resulting from a deletion of at least on constituent amino acid from FGF, any number of constituent amino acids may be lacking, as long as the properties of FGF are maintained.

In the mutein resulting from the replacement of at least one FGF-constituent amino acid by another, any number of FGF-constituent amino acids may be so replaced, as long as the properties of FGF are maintained.

Examples of constituent amino acids to be replaced include cysteine and others; cysteine however is preferred. Examples of constituent amino acids to be replaced, other than cysteine, include aspartic acid, arginine, glycine and valine.

When the constituent amino acid to be replaced is cysteine, it is preferable that the replacement amino acid be e.g. a neutral amino acid. Examples include glycine, valine, alanine, leucine, isoleucine, tyrosine, phenylalanine, histidine, tryptophane, serine, threonine and methionine; serine and threonine however are preferred.

When the constituent amino acid to be replaced is not cysteine, it is necessary to choose a replacement amino acid different from the constituent amino acid to be replaced, in such properties as hydrophilicity, hydrophobicity or electric charge. Specifically, when the amino acid to be replaced is aspartic acid, examples of the replacement amino acid include asparagine, threonine, valine, phenylalanine, and arginine; asparagine and arginine however are preferred.

When the amino acid to be replaced is arginine, examples of the replacement amino acid are glutamine, threonine, leucine, phenylalanine and aspartic acid; glutamine however is preferred.

When the constituent amino acid to be replaced is glycine, examples of the replacement amino acid include threonine, leucine, phenylalanine, serine, glutamic acid and arginine; threonine however is preferred.

When the constituent amino acid to be replaced is serine, examples of the replacement amino acid include methionine, alanine, leucine, cysteine, glutamine, arginine, and aspartic acid; methionine however is preferred.

When the constituent amino acid to be replaced is valine, examples of the replacement amino acid include serine, leucine, proline, glycine, lysine, and aspartic acid; serine however is preferred.

The preferred constituent amino acids to be replaced are aspartic acid, arginine, glycine, serine, and valine.

The preferred replacement amino acids are asparagine, glutamine, arginine, threonine, methionine, serine, and leucine.

In the replacement mutein, the constituent amino acid cysteine should ideally be replaced by serine.

In the above-mentioned replacement, two or more constituent amino acids may be replaced simultaneously; it is preferable that 2 to 3 constituent amino acids by replaced.

The mutein of the present invention may result from combination of 2 or 3 of the above additions, eliminations and replacements.

Site-directed mutagenesis may be employed to produce said mutein. This technology is widely known and described by R. F. Lather and J. P. Lecoq in "Genetic Engineering", Academic Press (1983), pp. 31-50. Oligonucleotide-directed mutagenesis is described by M. Smith and S. Gillam in "Genetic Engineering: Principles and Methods", Prenan Press (1981), vol. 3, pp 1-32.

To produce the structural gene which encodes said mutein:

(a) single-stranded DNA comprising a single strand of the FGF structural gene is hybridized with a mutant oligonucleotide primer (this primer is complementary to the region containing, for example, a cysteine codon to be replaced by the single strand, or, as the case may be, an antisense triplet which forms a pair with this condon, except for the discrepancy from amino acid encoding codons other than the above-mentioned condon, or, as the case may be, antisense triplets), (b) the primer is elongated using DNA polymerase to form a mutagenic heteroduplex, and (c) this mutagenic heteroduplex is replicated.

The phase DNA carrying the mutated gene is then isolated and inserted into a plasmid.

The plasmid thus prepared is used to transform an appropriate host; the transformant thus obtained is cultivated in medium to produce the desired mutein.

Examples of the muteins include those described in Biochemical and Biophysical Research Communications, vol. 151, pp. 701-708 (1988), European Patent Publication No. 281,822.

The method of the present invention is based on the principle of the sandwich technique, a noncompetitive method of immunochemical measurement.

Examples of carrier useful for the method of the present invention include gel grains such as agarose gels [e.g. Sepharose 4B, Sepharose 6B (produced by Pharmacia Fine Chemical, Sweden], dextran gels [e.g. Sephadex G-75, Sephadex G-100, Sephadex G-200 (produced by Pharmacia Fine Chemical, Sweden)] and polyacrylamide gels [e.g. Biogel P-30, Biogel P-60, Biogel P-100 (produced by Bio-Rad Laboratories, USA]; cellulose grains such as Avicel (produced by Asahi Chemical Industries, Japan) and ion exchange cellulose (e.g. diethylaminoethyl cellulose, carboxymethyl cellulose); physical adsorbents such as glass (e.g. glass balls, glass rods, aminoalkyl glass balls, aminoalkyl glass rods, silicon pieces, styrene resins (e.g. polystyrene balls, polystyrene grains), and immunoassay plates (e.g. plates produced by Nunc, Sweden); and ion exchange resins such as weakly acidic cation exchange resins [e.g. Amberlite IRC50 (produced by Rohm & Haas, USA), Zeo-Karb 226 (produced by Permutit AG, West Germany)] and weakly alkaline anion exchange resins [e.g. Amberlite IR-4B, Dowex 3 ; (produced by Dow Chemical, USA)].

Examples of heparins used for the method of the present invention include N-sulfuric acid-, N-acetyl-, and O-sulfuric acid-substituted products of polysaccharides comprising D-glucosamine, D-glucuronic acid and L-iduronic acid.

Known methods can be used to form the heparin coupled to a carrier, e.g. the method using poly-L-lysine, described by S. Suzuki et al. [Analytical Biochemistry, 137, 101 (1984)], a substance having a high affinity to heparin.

For example, poly-L-lysine (PLL) is immobilized on a 96-well plastic plate (e.g. produced by Dinatech, USA) at about 10 to 100 $\mu$g/well, or on glass beads, plastic beads or other carrier, Immobilization is achieved by reaction at about 4° to 15° C. overnight or at room temperature for 1 to 6 hr.

Heparin is then immobilized on the above-mentioned 96-well PLL immobilization plate at 100 $\mu$g to 1 mg/well. Immobilization is achieved by reaction at about 4° to 15° C. overnight or at room temperature for 1 to 6 hr.

Various commercially available antibody immobilization plates can also be used.

The antibody against FGF, used as a conjugate for the method of the present invention, may be polyclonal or monoclonal.

The polyclonal antibody against FGF can be produced by inoculating FGF as antigen to a warm-blooded animal to produce an anti-FGF antibody, which is then collected.

Any FGF can be used as the antigen, as long as it possesses biological or immunological activities similar to those of natural FGF; examples include FGF species produced by gene engineering technology and their fragments comprising a partial amino acid sequence essential to their biological or immunological activities. These FGF species produced by gene engineering technology may have additional Met at the polypeptide amino terminal, and may also be a mixture of an FGF and another FGF having additional Met at the amino terminal.

The above fragments can be produced by known routine methods of peptide synthesis, which may be based on a solid phase method of liquid phase method. Examples of such methods of peptide synthesis include the methods describe in "The Peptides", vol. 1 (1966), edited by Schröder and Lubke, Academic Press, New York, USA, "Peptide Synthesis (in Japanese)", edited by Izumiya et al., Maruzen (1975), and "Fundamentals and Experiments of Peptide Synthesis (in Japanese)", edited by Izumiya et al., Maruzen (1985).

These fragments may be produced by cleaving FGF using appropriate enzymes. Examples of such methods include the method described in "Biochemical Experiments Course 1, Protein Chemistry II (in Japanese)", edited by the Japanese Biochemical Society, Tokyo Kagaku Dojin (1976), pp. 255–332.

FGF as the antigen is coupled with carrier protein. Examples of the carrier protein include bovine tyroglobulin, bovine serum albumin, bovine gamma globulin, hemocyamin, and Freud's complete adjuvant (produced by Difco Laboratories).

Antigen FGF and carrier protein can be coupled by a standard method known to the art. Examples of coupling reagents include glutaraldehyde and water-soluble carbodiimide. The antigen FGF and the carrier protein should be coupled in a ratio of about 1 to 1 to about 1 to 10. Good results are often obtained when reaction is carried out at a nearly neutral pH level, ideally pH 6 to 8. reaction time is generally 1 to 12 hr. preferably to 2 to 6 hr. The complex thus formed may be dialyzed against water at 0° to 18° C. by a routine method, after which it may be frozen or lyophilized for storage.

To produce a polyclonal antibody, the immunogen thus produced is inocualted to a warm-blooded animal. Examples of warm-blooded animals which can be used to produce the above antibody include mammals (e.g. rabbits, sheep, goats, rats, mice, guinea pigs, bovines, horses, swine) and birds (e.g. chickens, doves, ducks, quails). The immunogen is inoculated to a warm-blooded animal in an amount such that efficient antibody production will occur; for example, antibodies are often produced when 1 mg of the immunogen, in an emulsion of 1 ml of a physiological saline solution containing Freund's complete adjuvant, is subcutaneously inoculated to a rabbit at the back and hind leg paw 5 times at 4-week intervals, The antibody thus formed in the warm-blooded animal is, for example, collected as follows: when a rabbit is used, blood is usually collected via ear vein between 7 and 12 days after the final inoculation, then centrifuged to yield a serum. The antiserum thus obtained is subjected to affinity chromatography using a carrier coupled with an antigen peptide; the fraction adsorbed to the column is recovered to separate a purified polyclonal antibody.

It is also possible to use the monoclonal antibody obtained in accordance with the method described by Milstein et al. [Nature, 256, 495 (1975)]. This monoclonal antibody is produced by immunizing a mammal with the antigen polypeptide or protein complex, fusing spleen cells excised from the animal and homo- or heterogenic lymphoid cells to yield a hybridoma, which is then cloned, inoculating the cloned hybridoma to a mammal to produce and accumulate a monoclonal antibody, which is then collected.

Immunization of e.g. mice can be achieved via any route, such as subcutaneous, intraperitoneal, intravenous, intramuscular, and intracutaneous administration; mainly subcutaneous, intraperitoneal, or intravenous (preferably subcutaneous) injection is recommended. Immunization interval immunization quantity etc. can also be widely varies so that various modes are possible; for example, in a method often used, immunization is conducted 2 to 6 times at 2-week intervals and spleen cells are excised and used 1 to 5 days, preferably 2 to 4 days after final immunization. It is desirable that the immunization quantity be over 1.0 μg, preferably 10 to 300 μg per mouse in each immunization, in terms of peptide. It is also desirable that partial blood sampling be conducted before spleen excision, to confirm increased blood antibody level, and that a cell fusion experiment be conducted using spleen cells.

For the cell fusion of spleen cells and lymphoid cells, excised mouse spleen cells are fused with a lymphoid cell line, such as an appropriate allo- or herterogenic (preferably allogenic) myeloma with a marker for hypoxanthineguaine-phosphoribosyl transferase deficiency (HGPRT−) or thymidine kinase deficiency (TK−) [e.g. P3-X63-Ag 8UI (Ichimori et al., Journal of Immunological Method, 80,55 (1985)]. Fusion can, for example, be achieved in accordance with the method of Köller and Milstein [Nature, 256, 495 (1975)]. for example, myeloma cells and spleen cells, in a ratio of about 1 to 5, are suspended in a medium prepared by mixing Iskov medium and Ham F-12 medium in a 1 to 1 ratio (herinafer referred to as IH medium), followed by cell fusion reaction in the presence of a fusogen such as Sendai virus or polyehtylene glycol (PEG). Dimethylsulfoxide (DMSO) and other fusion promoters can also be added. PEG with a degree of polymerization of 1000 to 6000 is normally used at a concentration of 10 to 80% for 0.5 to 30 minutes: efficient fusion is achieved, or example, by treating PEG 6000 at 35 to 55% for 4 to 10 minutes. The fused cells can be selectively prolifereated using hypoxanthine-aminopterin-thymidine medium (HAT medium, Nature, 256, 495 (1975)) etc.

The culture supernatant of the prolifereated cells can be screened for the desired antibody production; antibody titer screening can be conducted as follows: The culture supernatant is first examined for the production of antibody against the immunogen peptide by radioimmunoassay (RAI) or enzyme immunoassay (EIA). Various modifications are possible for these methods. An example of a preferred method of measurement based on EIA is described below. A carrier, such as cellulose beads, is coupled with e.g. rabbit anti-mouse immunoglobuline antibody by a routine method, the subject culture supernatant or mouse serum is added, followed by reaction at constant temperature (about 4 to 40° C.; the same applied below) for a given time. The reaction product is then thoroughly washed; an enzyme-labeled peptide (enzyme and peptide are coupled by a routine method, then purified) is added, followed by reaction at constant temperature for a given time. After the reaction product is thoroughly washed, an enzyme substrate is added, followed by reaction at a constant temperature for a given time; the formed coloring substance is then measured by optical absorbance, fluorescence intensity etc.

It is desirable that cells which proliferate in the selection medium in the wells, and in which antibody activities against the immunogen peptide are noted, be cloned by limited dilution analysis etc. The supernatent of the cloned cells is screened in the same manner to increase the number of cells with high antibody titer, to yield a hybridoma clone which produces a monoclonal antibody against the immunogen peptide.

The hybridoma thus cloned is proliferated in liquid medium. Specifically, the desired monoclonal antibody can be obtained from the culture both obtained by cultivating the hybridoma in a liquid medium, such as a medium prepared by adding about 0.1~40% bovine serum to RPMI-1640 medium [Moore, G. E. et. al., Journal of American Medical Association, 199, 549 (1967)] for 2 to 10 days, preferably 3 to 5 days. The antibody can also be obtained by intraperitoneally inoculating the hybridoma to a mammal for cell proliferation, and collecting the ascites fluid. For this purpose, when mice are used, for example $1 \times 10^4$ to $1 \times 10^7$, preferably $5 \times 10^5$ to $\times 10^6$ hybridoma cells are intraperitoneally inoculated to each mouse of BALB/c or other lines, previously inoculated with mineral oil etc.; ascites fluid is then collected 7 to 20 days, preferably 10 to 14 days after inoculation. The antibody produced and accumulated in the ascites fluid can easily be isolated in the form of pure immunoglobuline by e.g. ammonium sulfate fractionation and DEAE-cellulose column chromatography.

The antibody molecule may be IgG, or its fragment [e.g.F(ab')$_2$, FAb', Fab'', or FAb]. It is preferable however that the antibody molecule to be coupled directly with a labeling agent be Fab'.

Examples of labeling agents for RIA include $^3$H, $^{125}$I and other radioisotopes.

Examples of labeling agents for EIA include enzymes, fluorescent substances and luminescent substances; the use of enzyme is recommended. Stable enzymes with high specific activity are preferred; peroxidase, alkaline phosphatase, $\beta$-D-galactosidase, glucose oxidase etc. can be used; peroxidase is preferred. Peroxidase of various derivations can be used; examples include peroxidase derived from horseradish, pinapple, fig, sweet potato, kidney bean, corn etc.; horseradish peroxidase (HRP) is preferred.

Examples of fluorescent substances include FITC (fluorescein isothiocyanate), rhodamine, and lanthanide chelate.

Examples of luminescent substances include acridinium esters.

To couple the antibody with a labeling agent, known routine methods cab be used; for example, $^{125}$I can be coupled to the antibody. Examples of known routine methods which can be used include the method using an iodogen, described by K. M. Furguson et al., [Acta Endocrinal. Supple, 225 130 (1979)].

The subject sample to be measured using the measurement system of the present invention includes urine, serum, plasma, cerebrospinal fluid and other body fluids, or cell of bacterial extracts or their culture supernatants.

An example of EIA for the measurement method of the present invention, when peroxidase is used as the labeling agent, is described in detail below; such use of peroxidase however is not to be construed as a limitation for the present invention.

① The FGF- containing sample to be measured is added to carrier-coupled heparin, followed by reaction with a peroxidase-labeled antibody.

② A peroxidase substrate is added to the reaction produce obtained in ①; the optical absorbance or fluorescence intensity of the resulting substance is then determined, to calculate the enzyme activity of the above reaction product.

③ Separately, procedures ① and ② above are followed for a known amount of FGF standard solution to draw a standard curve showing the relationship between FGF and absorbance of fluorescence intensity.

④ The absorbance or fluorescence intensity obtained for the subject of analysis (subject sample), which contains an unknown amount of FGF, is applied to the standard curve to determine the amount of FGF in the subject of analysis.

An example of RIA for the measurement method of the present invention, when $^{125}$I is used as the labeling agent, is described in detail below: Such use of $^{125}$I however is not to be construed as a limitation for the present invention.

① The FGF-containing sample to be measured is added to carrier-coupled heparin, followed by reaction with a $^{125}$I-labeled antibody (two causes: $^{125}$I is coupled directly to the anti-FGF antibody, or a nonlabeled anti-FGF antibody is used in combination with a $^{125}$I-labeled secondary antibody).

② The $\gamma$-radioactivity of the reaction produce obtained in ① is measured.

③ Separately, procedures ① and ② above are followed for a known amount of FGF standard solution to draw a standard curve showing the relationship between FGF and $\gamma$- radioactivity.

④ The $\gamma$-radioactivity obtained for the subject of analysis (subject sample), which contains an unknown amount of FGF, is applied to the standard curve to calculate the amount of FGF in the subject of analysis.

This method provides an efficient means of detecting and measuring FGF in clinical specimens (e.g. blood, serum, plasma, urine, pleural effusion, cerebrospinal fluid), and of investigating the distribution of FGF in tissues and organs.

Using heparin as a conjugate carried by a carrier, the method of the present invention permits measurement of blood FGF to high sensitivity; this method is also applicable to diagnosis of tumor.

Abbreviations for amino acids etc. used in the present specification are based on abbreviations specified by the IUPAC-IUB Commission on Biochemical Nomenclature or those commonly used in relevant fields; some examples are given below. Note that when an optical isomer of amino acid is present, it is an L-body, unless otherwise stated.

Tyr: Tyrosine
Nle: Norleucine

The present invention will now be describe in more detail by means of the following examples, although these are not to be construed as limiting the present invention.

EXAMPLE 1

Figure 1:
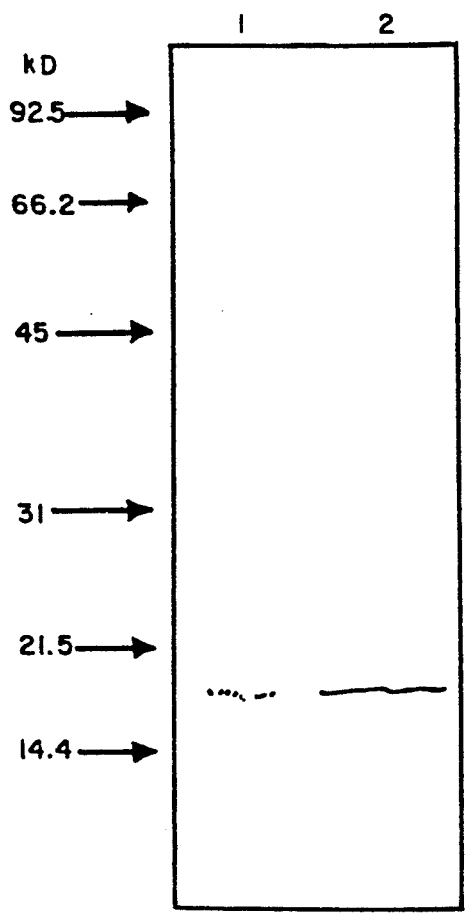
FIG. 1 shows the results of western blotting of the anti-[Tyr$^{11}$] human bFGF(1-11) Nle$^{12}$ rabbit antibody obtained in Example 1(1).
Figure 2:
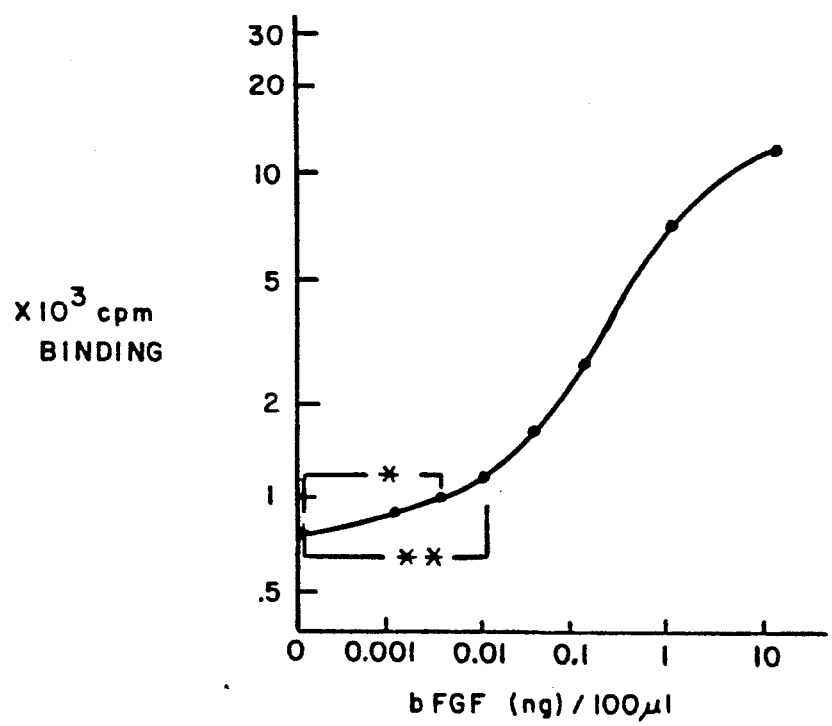
FIG. 2 shows the standard curve of RIA using recombinant-derived bovine bFGF, obtained in Example 1 (2).

(1) Preparation of anti-[Tyr$^{11}$] human bFGF (1-11) Nle$^{12}$ rabbit antibody The peptide [Tyr$^{11}$] human bFGF (1-11) Nle$^{12}$ [produced in the same manner as described in "Peptide Synthesis", M. Bodanszky, Y. S. Klausner, and M. A. ondetti, John Weily and Sons, N. Y. (1976); purchased from Alberta Peptide Institute, Edmonton Alberta, Canada] was bound with KLH (Keyhole Limpet Hemocyanin) using glutaraldehyde; this conjugate was dissolved in a phosphate buffer solution (PBS) (800 mg/l NaCl, 200 mg/l KCl, 2160 mg/l NaHPO$_4$·7H$_2$O, 200 mg/l KH$_2$PO$_4$, 100 mg/l MgCl$_2$·6H$_2$O) to a peptide concentration of 100 μg/ml; this solution was mixed with an equal amount of Freund's complete adjuvant (Difco Laboratories). 1 ml of this mixture was intradermally administerered to rabbits; a mixture of 100 μg/ml of the above-mentioned synthetic peptide and an equal amount of incomplete adjuvant (Difco Laboratories) was the administered at 2-week intervals. After 5 adiministrations, blood was collected and dept standing at room temperature for 5 hr, then left at 4° C. for 16 hr. after which it was centrifuged at 300 rpm for 10 min; the supernatant was used as anti-[Tyr$^{11}$] human bFGF (1-11) Nle$^{12}$ rabbit serum. Also, 0.5 g of cyanogen bromide-activated Sepharose 4B (Pharmacia) was transferred to a glass filter and sufficiently expanded with 20 ml of 0.001 N HCl, after which it was thoroughly washed with 400 ml of the same aqueous hydrochloric acid. Separately, 2 ml of a solution of 0.1M sodium bicarbonate and 0.5M sodium chloride was added to 100 μl of a solution of the peptide [Tyr$^{11}$] human bFGF (1-11) Nle$^{12}$ (protein content, 40 mg/ml); this mixed solution was adjusted to pH 8.4 with a solution of 0.1M sodium hydroxide. To this solution, the above-mentioned cyanogen bromide-activated Sepharose 4B was added, followed by reaction at room temperature for 2 hr. After reaction, the gel was transferred to a glass filter and washed with 100 ml of a solution of 0.1M sodium bicarbonate and 0.5M sodium chloride. The gel was then added to 10 ml of a solution of 0.1M tris-HCl, pH 8.0; reaction was carried out at 4° C. for 20 hr while stirring the solution gently to mask the remained active groups. The gel was then washed with sequential additions of a 0.1M acetate buffer solution containing 1M sodium chloride (pH 4.0) and a 0.1M borate buffer solution containing 1M sodium chloride (pH 8.0), each in 100 ml amount. The gel was then suspended in PBS and stored in column at 4° C.

The above-mentioned serum was applied to this column; the column was then thoroughly washed with PBS so that optical absorption at 280 nm disappeared. Elution was then conducted with a 0.2M glycine-HCl buffer solution (pH 2.3) containing 10% dioxane; the eluted fraction was immediately neutralized with a one-third its amount of 1M Tris-HCl, pH 7.4. This solution was dialyzed against PBS at 4° C. for 16 hr, after which it was centrifuged at 10,000 rpm for 10 min; the supernatant was used as anti-[Tyr$^{11}$] human bFGF (1-11) Nle$^{12}$ rabbit antibody.

To evaluate the specificity of the antibody, the heparin-coupled protein in the culture supernatant of bovine corneal endothelial cells (BCE cell) and recombinant bFGF was subjected to SDS-PAGE, followed by western blotting a specific band (lane 1) was detected at the position corresponding to bFGF (lane 2) (see FIG. 1).

(2) Two-site radioimmunoassay (RIA) using heparin-coated microtiter plate

The following procedures were followed using a 96-well flat-bottomed polyvinyl chloride microtiter plate (Dynatech Laboratories, Alexandria, Va., USA). The plate was washed with a phhysiological saline solution/0.1% Tween 20, rinsed with distilled water, treated with ethanol, and thoroughly dried to eliminate well-to-well differences.

Poly-L-lysine (produced by Sigma Co.) was dissolved in distilled water to 100 μg/ml; this solution was transferred to the above plate at 100 μl/well. The plate was left at 4° C. overnight; the solution was then discarded, and each well was washed with distilled water; the plate was thus coated with poly-L-lysine.

Subsequently, heparin (produced by Sigma Co.) was dissolved in distilled water to 1 mg/ml; this solution was transferred to the above plate coated with poly-L-lysine at 100 μl/well. The plate was left at 4° C. overnight; the solution was then discarded, and each well was washed with distilled water; the plate was thus coated with heparin.

To each well of this plate, 200 l of 1% bovine serum albumin (BSA)/PBS was added; the plate was left at 4° C. overnight; the solution was then discarded; the plate was then washed with 0.5M NaCl/PBS to remove the protein nonspecifically bound with heparin. The plate thus blocked was used for RIA as follows:

The sample, appropriately diluted with 0.1% BSA/PBS, was transferred to the plate at 100 μl/well, and left at 4° C. overnight. To obtain background values, a well containing 0.1% BSA/DMEM/25mM Tris-HCl (pH 7.4) or 0.1% BSA/10 mM MgCl$_2$/25 mM Tris-HCl (pH 7.4) was also prepared. DMEM: Dulbecco's modified Eagle's medium.

After sample adsorption to the plate, each well was washed with 0.1% BSA/PBS/10 mM MgCl$_2$; the anti-[Tyr$^{11}$] human bFGF (1-11) Nle$^{12}$ rabbit antibody described in Example 1 (1), in dilution with 0.1% BSA/PBS/10 mM MgCl$_2$ to a 1×10$^{-4}$ to 2×10$^{-5}$ concentration was added to the plate at 100 μl per well; the plate was left at 4° C. overnight.

After further plate washing with 0.1% BSA/PBS/10 mM MgCl$_1$, $^{125}$I-anti-rabbit IgG goat antibody Fab" (produced by Miles Co.), in dilution with 0.1% BSA/PBS to a 1000- to 5000-fold volume, was added to the plate at 100 μl per well; the plate was left at 4° C. overnight. After thorough plate washing with 0.1% BSA/PBS/1 mM MgCl$_2$, each well was cut out with scissors; the count from each well was taken using a gamma counter. The standard curve obtained by this RIA procedure, using recombinant-derived bovine bFGF, is shown in FIG. 1 (N=4, m±SD,*P<0.05,**P<0.01). This curve shows that 1 to 10 pg of bFGF can be detected. Note that the recombinant-derived bovine bFGF was purchased from Amgen Co., USA.

Figure 3:
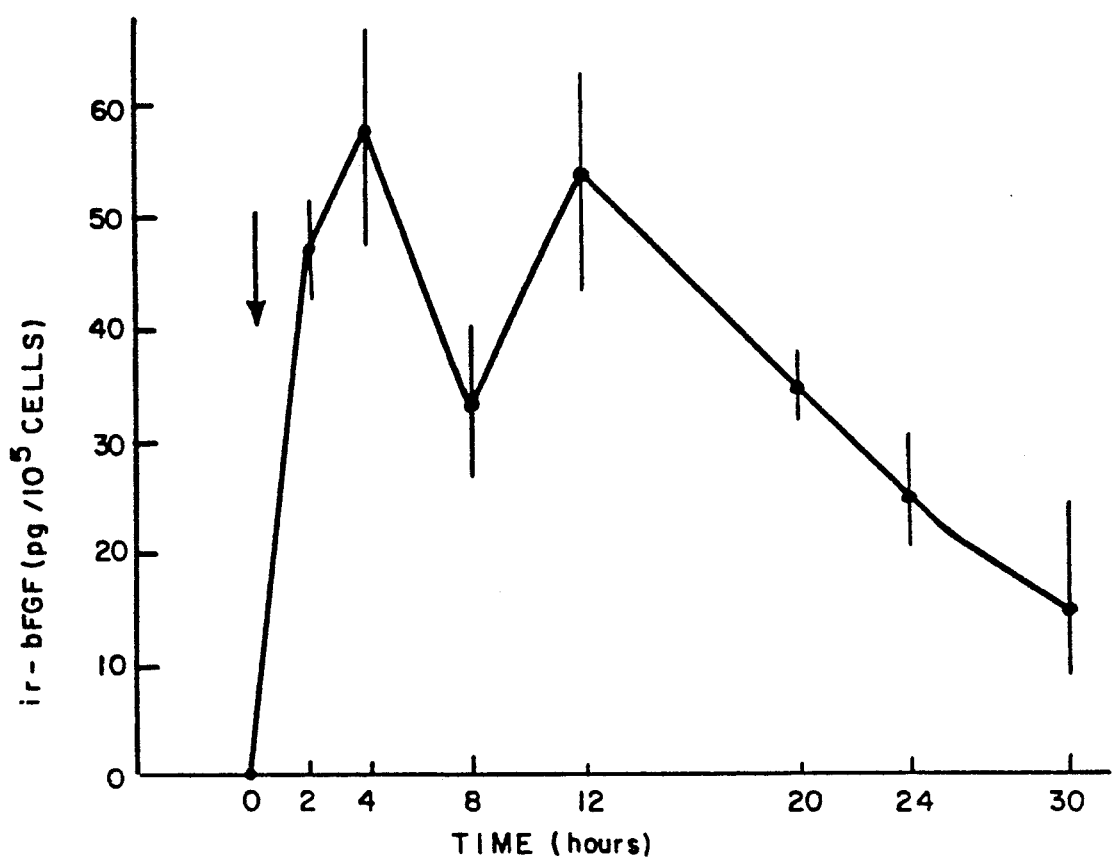
FIG. 3 shows the amount of bFGF in bovine corneal endothelial cell culture broth, determined in Example 1 (2).
Figure 4:
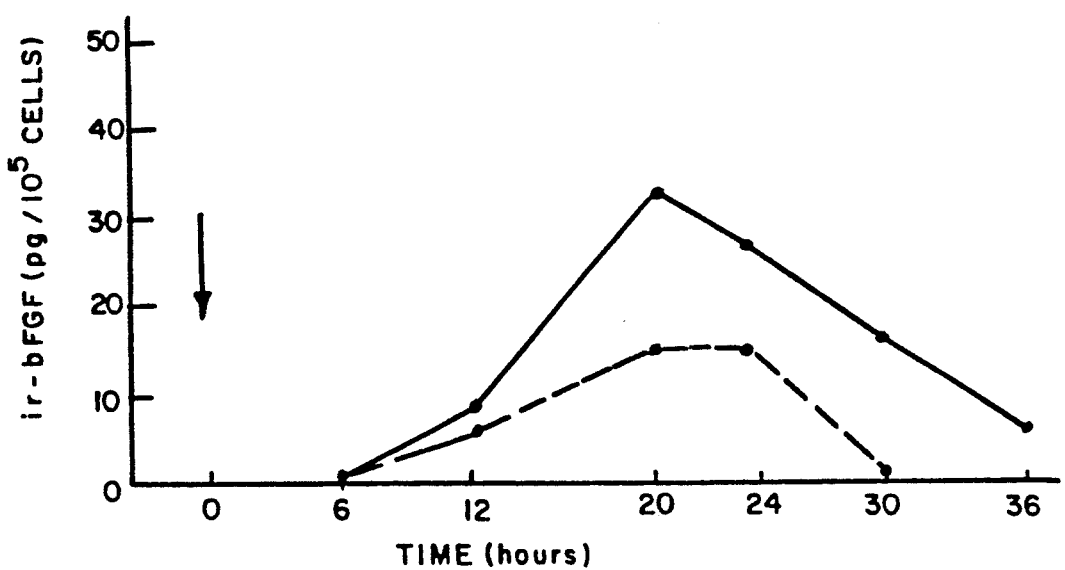
FIG. 4 shows the amount of bFGF in BCE cell culture broth, determined in Example 1 (2).

When bovine corneal endothelial cells (BCE cells) were cultivated in serum-free medium in the same manner as above, the amount of bFGF released into culture broth followed the time course shown in FIG. 3 (n=3, m±SE).

bFGF, released by stimulating BCE cells with epithelial cell growth factor (EGF) in the same manner as above, could also be detected (FIG. 4).

Figure 5:
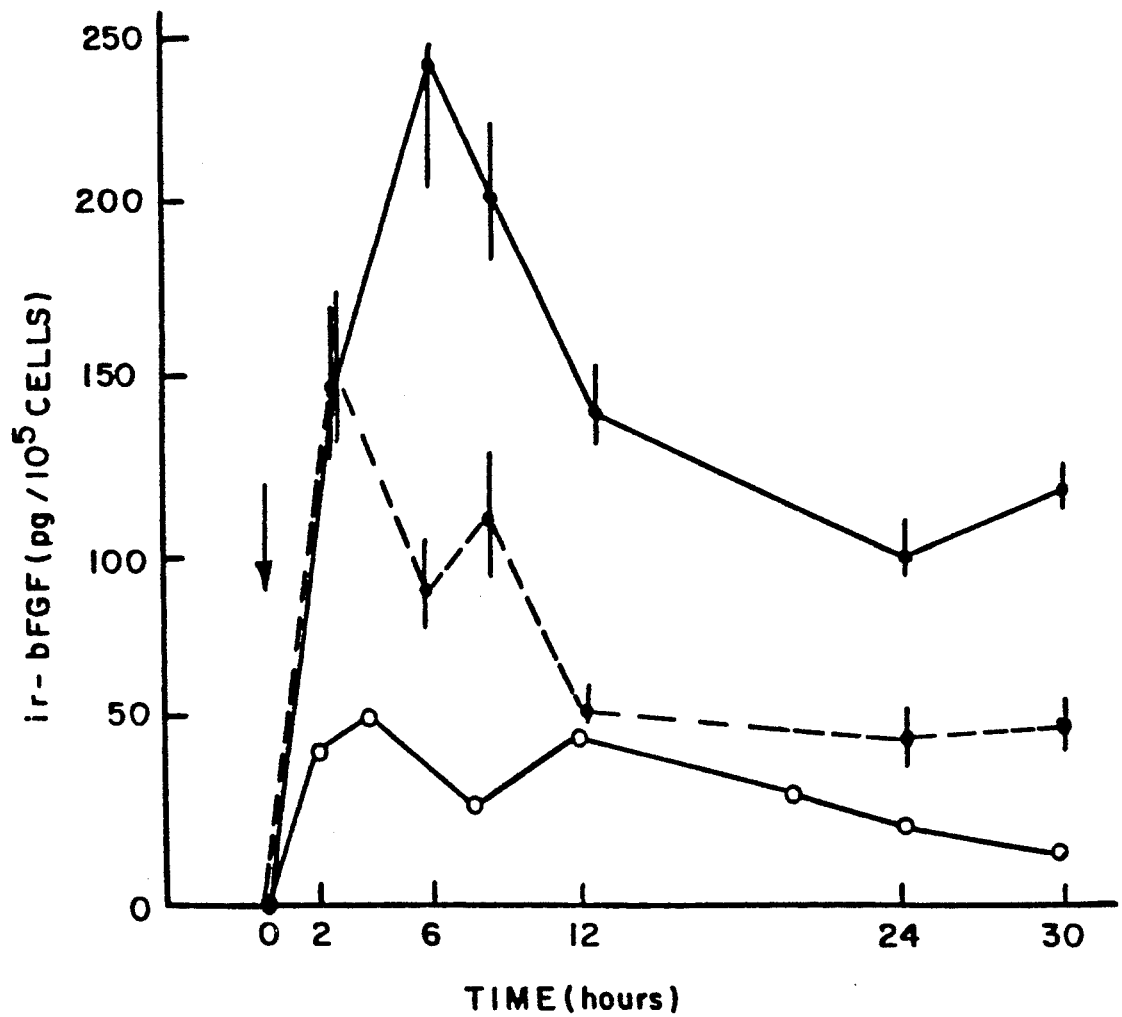
FIG. 5 shows the amount of bFGF in human cancer cell culture broth, determined in Example 1 (2).

It was also possible to detect bFGF released during cultivation of the human cancer cell line U87MG in serum-free medium in the same manner as above (FIG. 5, n=3, m±SE).

Figure 6:
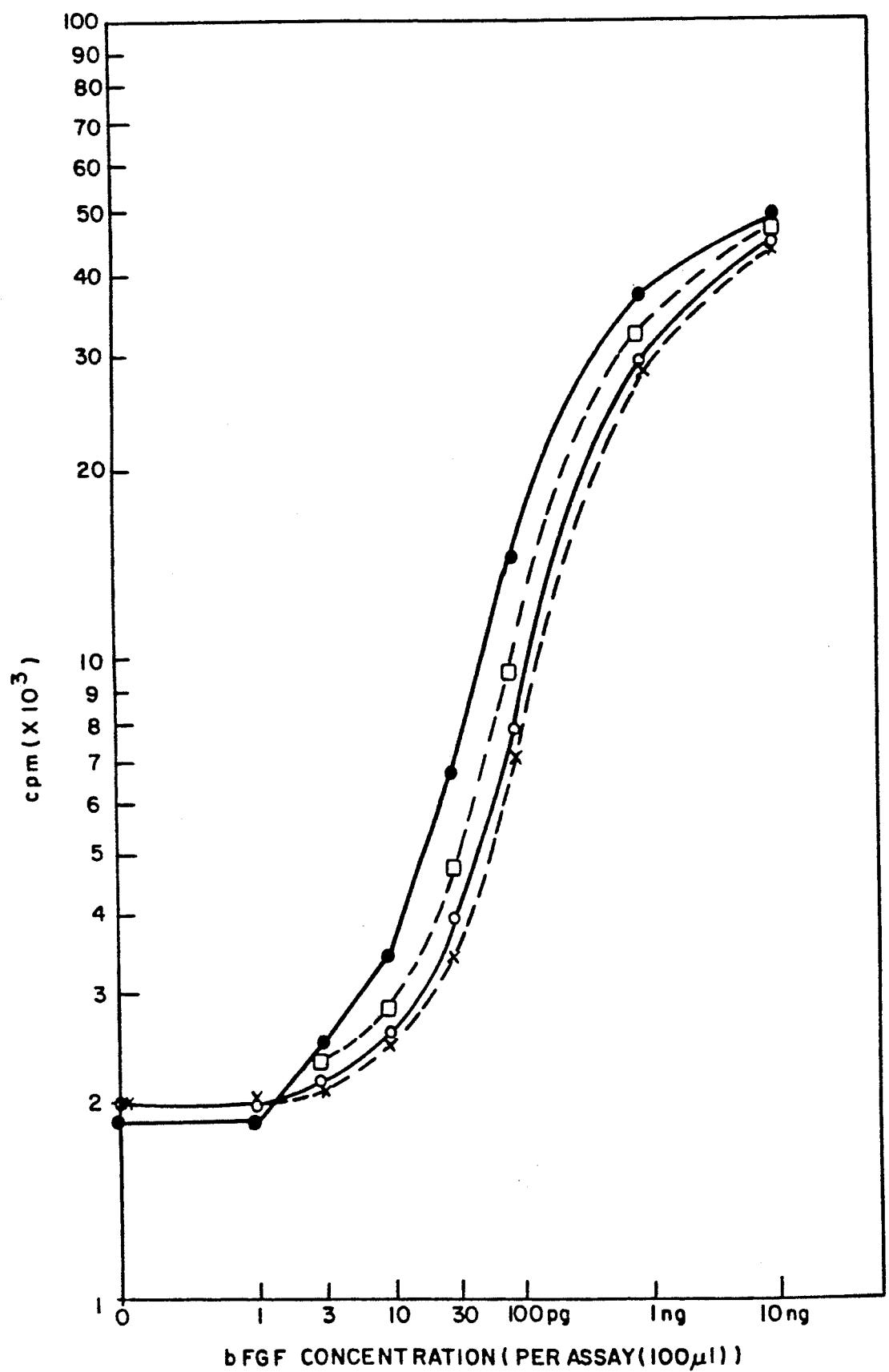
FIG. 6 shows the effect of serum on measurement of bFGF, determined in Example 1 (2).

FIG. 6 shows the effect of serum on the present RIA technique, obtained in the same manner as above, where PLL (poly-L-lysine) was used at 300 μg/ml, and heparin at 10 mg/ml. In FIG. 6, —□—, —○—, and —×— respectively show the results for 5% FCS, 10% FCS, and 20% FCS.

What we claim is:

1. A method for detecting and/or measuring fibroblast growth factor (FGF), which comprises subjecting a sample to a sandwich technique using heparin coupled to a carrier and an antibody labeled with a labeling agent said fibroblast growth factor coupling to said heparin and said labelled antibody coupling to said fibroblast growth factor.

2. A method as claimed in claim 1, wherein the FGF is a basic FGF.

3. A method as claimed in claim 2, wherein the basic FGF is human basic FGF.

* * * * *